US012484910B2

(12) United States Patent
Ninomiya

(10) Patent No.: US 12,484,910 B2
(45) Date of Patent: Dec. 2, 2025

(54) ENDOSCOPIC TREATMENT TOOL

(71) Applicant: ZEON CORPORATION, Tokyo (JP)

(72) Inventor: Masakazu Ninomiya, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 246 days.

(21) Appl. No.: 18/552,425

(22) PCT Filed: Mar. 23, 2022

(86) PCT No.: PCT/JP2022/013564
§ 371 (c)(1),
(2) Date: Sep. 25, 2023

(87) PCT Pub. No.: WO2022/210174
PCT Pub. Date: Oct. 6, 2022

(65) Prior Publication Data

US 2024/0173037 A1 May 30, 2024

(30) Foreign Application Priority Data

Mar. 31, 2021 (JP) ................................ 2021-061472

(51) Int. Cl.
*A61B 17/128* (2006.01)

(52) U.S. Cl.
CPC ................................ *A61B 17/1285* (2013.01)

(58) Field of Classification Search
CPC ............ A61B 17/1285; A61B 17/1227; A61B 2017/00367
See application file for complete search history.

(56) References Cited

U.S. PATENT DOCUMENTS 4,467,802 A 8/1984 Maslanka
8,419,751 B2 4/2013 Harada et al.
(Continued)

FOREIGN PATENT DOCUMENTS

EP 3689254 A1 8/2020
EP 3714758 A1 9/2020
(Continued)

OTHER PUBLICATIONS

Extended European Search Report issued in European Patent Application No. 22780389.7, dated Feb. 12, 2025 in 9 pages.
(Continued)

*Primary Examiner* — Ryan J. Severson
(74) *Attorney, Agent, or Firm* — Knobbe, Martens, Olson & Bear, LLP

(57) ABSTRACT

Provided is an endoscopic treatment tool. The base has a guide groove extending in the axial direction and both side walls of the guide groove, and a plurality of positioning engagement portions that can engage the slider concavo-convexly at a plurality of locations in the axial direction. The slider has, inside a cylindrical body of a predetermined length surrounding the base, a wire fixing portion which is slidably guided into the guide groove and to which the proximal end of the drive wire is fixed, and the protruding portion that is concavo-convexly engaged with one of a plurality of positioning engagement portions when the slider reaches one of a plurality of axial locations with respect to the base. The spring portion with cantilevered structure is integrally provided on the base to elastically engage the plurality of positioning engagement portions of the base with the protruding portion of the slider concavo-convexly.

8 Claims, 19 Drawing Sheets

(56) References Cited

U.S. PATENT DOCUMENTS

| | | | |
|---|---|---|---|
| 2006/0224165 | A1 | 10/2006 | Surti et al. |
| 2006/0259049 | A1 | 11/2006 | Harada et al. |
| 2016/0213375 | A1 | 7/2016 | Rosenberg et al. |

FOREIGN PATENT DOCUMENTS

| | | | |
|---|---|---|---|
| JP | 10-118013 | A | 5/1998 |
| JP | 2008-516734 | A1 | 5/2008 |
| JP | 2008-532637 | A | 8/2008 |
| JP | 2010-81970 | A | 4/2010 |
| JP | 2012-200518 | A | 10/2012 |
| JP | 6432175 | B2 | 12/2018 |
| WO | WO 2006/044865 | A2 | 4/2006 |
| WO | WO 2004/082488 | A1 | 6/2006 |
| WO | WO 2020/095427 | A1 | 5/2020 |
| WO | WO 2020/105253 | A1 | 5/2020 |
| WO | WO 2020/136701 | A1 | 7/2020 |
| WO | WO 2019/066084 | A1 | 11/2020 |

OTHER PUBLICATIONS

International Search Report and Written Opinion of the International Searching Authority for International Application No. PCT/JP2022/010471, mailed on May 17, 2022, in 7 pages.

International Search Report for International Application No. PCT/JP2022/010471, mailed on May 17, 2022 (English translation), in 2 pages.

International Search Report and Written Opinion of the International Searching Authority for International Application No. PCT/JP2022/013564, mailed on Jun. 7, 2022, in 7 pages.

International Search Report for International Application No. PCT/JP2022/013564, mailed on Jun. 7, 2022 (English translation), in 2 pages.

ENDOSCOPIC TREATMENT TOOL

CROSS-REFERENCE TO RELATED APPLICATIONS

This application is the U.S. National Phase under 35 U.S.C. § 371 of International Application PCT/JP2022/013564, filed Mar. 23, 2022, which claims priority to JP Application No. 2021-061472, filed Mar. 31, 2021.

FIELD OF THE INVENTION

The present invention relates to an endoscopic treatment tool for performing treatment such as hemostasis using an endoscope.

BACKGROUND ART

A clip device as an endoscopic treatment tool is a device used for detaining a clip placed at the tip of a sheath that is passed through a treatment tool guide tube of an endoscope in a state of clipping internal tissue for purposes of such as hemostasis and marking. The clip is configured to be separable with respect to the sheath, and generally a connection hook that is engageable and disengageable with respect to a connection portion formed at a rear end of the clip is attached at a distal end portion of a drive wire passed through the sheath.

As connection hooks that are engageable and disengageable with respect to the connecting portion of the clip, various methods have been developed so far. In particular, the connection hook, which is biased forward by its own elasticity into a substantially V-shaped open state and whose tip is bent inward, is widely used because it has a simple structure and can be connected to the clip and the connection and separation operation with respect to the clip is reliably performed with a good performance.

As such a clip device, for example, one described in Patent Document 1 below is known. A connection hook for clipping the clip is connected to the distal end of the drive wire, which passes through the inner sheath and is connected at its proximal end to the slider. The inner sheath is passed through the outer sheath and connected at its proximal end to a base.

When a slider is slid in the distal direction of the base to set to a clip release position (open position), the connection hook protrudes from the tip of the inner sheath and becomes a substantially V-shaped open state. From this state, when the slider is slid by a predetermined amount in the direction of approaching the base (retracting direction) and set to a clip connection position (neutral position), the connection hook enters the inner sheath, the connection hook closes, and the clip can be in a connected (clipped) state. From this state, when the slider is further slid in the direction of approaching the base and set to a clip fastening position (fire position), the connection hook clipping the clip further enters the inner sheath and a fastening ring attached to the clip is slid distally by the tip of the inner sheath to bring the clip into a fastened state in which the clip is closed and fixed. After that, by setting the slider to the open position again, the clip of the fastened clip by the connection hook can be released.

As the drive wire, a wire rope made of a single wire or a twisted wire made by spirally winding a plurality of wires (element wires) is used. In addition, hollow tubes made of resin are used as the inner sheath through which the drive wire is passed through and the outer sheath through which the inner sheath is passed through. For example, it is possible to use a hollow tube made of resin such as polyethylene as the outer sheath, and a close-wound coil sheath as the inner sheath.

CITATION LIST

Patent Literature

[Patent Document 1] Japanese Patent Application Publication No. 2012-200518

SUMMARY OF THE INVENTION

Technical Problem

The endoscopic treatment tool disclosed in Patent Document 1 has a plate spring and a pair of spring housing sections that accommodate the plate spring inside the slider to position the slider in the three positions described above, which are the open position, the neutral position, and the fire position.

However, the endoscopic treatment tool according to the prior art has the problems that the use of the plate spring increases the number of parts constituting the slider, and the size of the slider increases due to the provision of the spring accommodating portion for accommodating the plate spring.

The present invention has been made in view of the above problems, and an object of the present invention is to provide an endoscopic treatment tool in which the number of parts constituting the slider is reduced and the slider is downsized.

Means to Solve the Problem

To achieve the above-mentioned purpose, an endoscopic treatment tool of the present invention comprises: a tubular sheath: a drive wire passed through the sheath: a connection hook connected to the distal end of the drive wire: a base connected to the proximal end of the sheath: and a slider to which the proximal end of the drive wire is connected and which is slidably held against the base in the axial direction of the sheath and the drive wire, the endoscopic treatment tool removably holding a treatment component by means of the connection hook, wherein the base has a guide groove extending in the axial direction and both side walls of the guide groove, and has a plurality of positioning engagement portions that can engage the slider concavo-convexly at a plurality of locations in the axial direction, the slider has, inside a cylindrical body of a predetermined length surrounding the base, a wire fixing portion which is slidably guided into the guide groove and to which the proximal end of the drive wire is fixed, and a concavo-convex engagement portion that is concavo-convexly engaged with one of the plurality of positioning engagement portions when reaching one of the plurality of axial locations relative to the base, and a spring portion with cantilevered structure is integrally provided on at least one of the base and the slider to elastically engage at least one of the plurality of positioning engagement portions of the base and the concavo-convex engagement portions of the slider concavo-convexly with respect to the other.

According to the above configuration, the endoscopic treatment tool according to the present invention is provided with the spring portion with cantilevered structure integrally with at least one of the base and the slider. Therefore, compared to conventional products that use a plurality of separate plate springs, and the like, downsizing and simplification of structure by reducing the number of parts is possible, thereby allowing the number of assembly man-hours to be reduced, so that the manufacturing cost can be reduced. Further, in the endoscopic treatment tool according to the present invention, the spring portion with cantilevered structure can be formed integrally with at least one of the base and the slider, so that the spring portion with cantilever structure can be integrally formed by resin or the like. For this reason, the elastic concavo-convex engagement state of the plurality of positioning engagement portions of the base and concavo-convex engagement portions of the slider via the spring portion with cantilevered structure and the corresponding strength (gentle or steep) of the slider's operating resistance can be easily and accurately set according to changes in the slide position. Therefore, it is possible to clarify the operation feeling of the slider with respect to the base and the corresponding operation sound, facilitate the operation of the slider related to attachment and detachment of the treatment component by the connection hook, and clarify the operation position.

Further, in the endoscopic treatment tool according to the present invention, the wire fixing portion and the concavo-convex engaging portion of the slider are formed at different positions from each other in the axial direction of the cylindrical body, and when the concavo-convex engagement portion of the slider engages any of the plurality of positioning engagement portions of the base, the wire fixing portion of the slider is slidably guided into the guide groove avoiding the positioning engagement portion of the plurality of positioning engagement portions that engages the concavo-convex engagement portion.

According to the above configuration, in the endoscopic treatment tool according to the present invention, when the spring portion with cantilevered structure bends to engage the concavo-convex engagement portion of the slider with one of the plurality of positioning engagement portions of the base, the wire fixing portion of the slider is slidably guided avoiding the positioning engagement portion that engages the concavo-convex engagement portion of the plurality of positioning engagement portions. In other words, the positions of the concavo-convex engagement portion and the wire fixing portion are set so that the slider can slide against the base while considering the flexure of the spring portion. Therefore, even if the flexure range of the spring portion with cantilevered structure is set to the inner side of the radial direction, the flexure of the spring portion with cantilevered structure does not impair the guiding function of the slider, thereby making it possible to reduce the diameter of the device while simplifying the structure.

Further, in the endoscopic treatment tool according to the present invention, the spring portion of cantilevered structure may be provided on at least one side of both side wall portions of the guide groove of the base, to be adjacent to the plurality of positioning engagement portions.

According to the above configuration, the endoscopic treatment tool according to the present invention can be easily arranged with the operation cam surface which applies an operation resistance corresponding to the sliding position of the slider to the outer surface side the spring portion with cantilevered structure forming the guide groove on the inner surface side to clarify the operation position.

Further, in the endoscopic treatment tool according to the present invention, the wire fixing portion and the concavo-convex engagement portion of the slider may be configured to protrude inwardly in the radial direction of the cylindrical body so as to cross each other.

According to the above configuration, in the endoscopic treatment tool according to the present invention, the flexure range of the spring portion with cantilever structure can be set radially inward, and the diameter of the device can be reduced.

Further, in the endoscopic treatment tool according to the present invention, for each of the plurality of positioning engagement portions of the base, a spring portion with cantilevered structure may be provided on both sides of the axial direction, and each positioning engagement portion may be configured to be formed by the opposing free end portions of the spring portion with cantilevered structure on one side in the axial direction and the spring portion with cantilevered structure on the other side in the axial direction.

According to the above configuration, in the endoscopic treatment tool according to the present invention, each positioning engagement portion of the base is formed by the opposing free end portions of the spring portions with cantilevered structure on both sides in the axial direction. Therefore, it is possible to accurately set the operation resistance according to the sliding position of the slider of the spring portion with cantilevered structure, and to obtain a good operation feeling and operation sound.

Further, in the endoscopic treatment tool according to the present invention, the spring portion with cantilevered structure on one side of the axial direction and the spring portion with cantilevered structure on the other side of the axial direction corresponding to the respective positioning engagement portions of the base may have a curved convex surface protruding toward the inner wall of the cylindrical body of the slider on the respective free end portion side.

According to the above configuration, in the endoscopic treatment tool according to the present invention, the spring portions with cantilever structure on both sides in the axial direction corresponding to the plurality of positioning engagement portions of the base have a curved convex surface that protrudes toward the inner wall surface of the mating hole of the cylindrical body of the slider on the respective free end portions sides, so that it is possible to stabilize the guide function of the cylindrical body of the slider and improve the operation feeling.

Further, in the endoscopic treatment tool according to the present invention, the spring portion with cantilevered structure may be provided adjacent to the concavo-convex engagement portion of the slider.

According to the above configuration, in the endoscopic treatment tool according to the present invention, since the slider is provided with the spring portion with cantilevered structure, the degree of freedom in setting the length of the spring portion is increased, so that the operation feeling of the slider is enhanced. In addition, it is no longer necessary to provide a spring portion on the base side, so that the flexibility of the shape can be increased.

Further, in the endoscopic treatment tool according to the present invention, the cylindrical body of the slider may have a pair of split cylindrical portions, which are opposed to each other in the direction of the depth of the guide groove in the base and are mutually engaged at one end in the axial direction, and a short cylindrical portion that joins the pair of split cylindrical portions at the other end in the axial direction, the pair of split cylindrical portions may comprise the wire fixing portion holding the proximal end of the drive wire, and the short cylindrical portion may comprise the concavo-convex engagement portion that concavo-convexly engages with any of the plurality of positioning engagement portions of the base.

According to the above configuration, in the endoscopic treatment tool according to the present invention, the cylindrical body can be made of resin molding, and the work of fixing the drive wire can be facilitated.

DETAILED DESCRIPTION OF EMBODIMENTS

Figure 1:
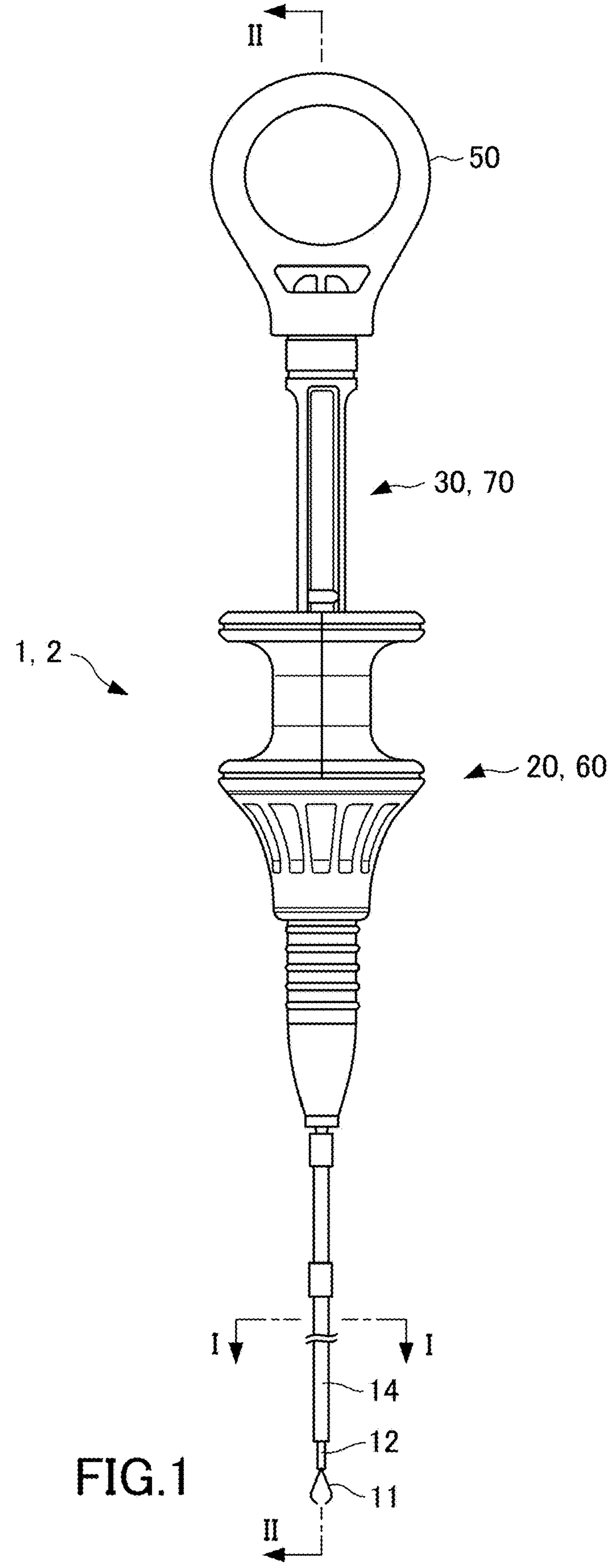
FIG. 1 shows a front view of an endoscopic treatment tool according to the first embodiment of the present invention.
Figure 2:
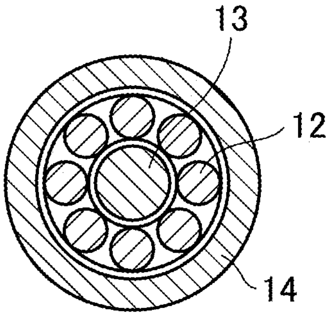
FIG. 2 shows a I-I cross-sectional view of FIG. 1.
Figure 3A:
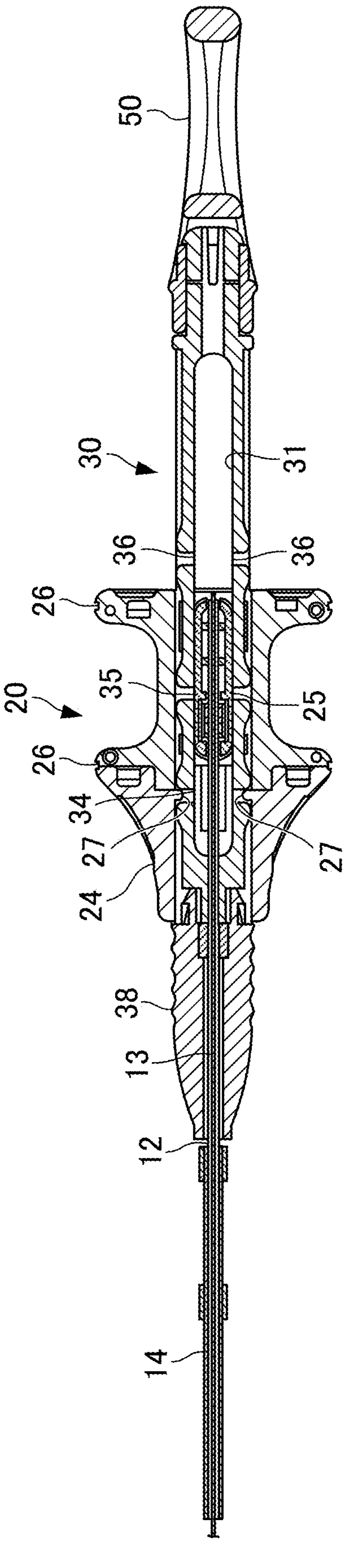
FIG. 3A shows a II-II cross-sectional view of FIG. 1.
Figure 3B:
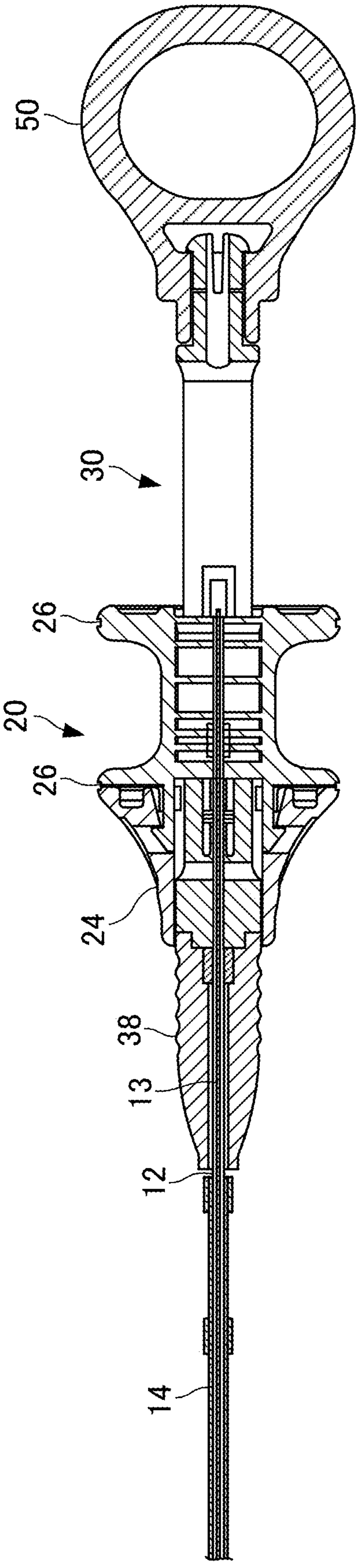
FIG. 3B shows a cross-sectional view perpendicular to the II-II cross-section of FIG. 1.

The following is a description of the embodiment of a clip device as an endoscopic treatment tool of the present invention. In order to make the structure of each part of the device easier to understand, the relative size of each part in each drawing does not necessarily correspond to the size in the actual device.

First Embodiment

As shown in FIGS. 1, 2, 3A, and 3B, the clip device 1 according to the first embodiment of the present invention is generally composed of a connection hook 11, an inner sheath 12, a drive wire 13, an outer sheath 14, a slider 20, a base 30, and an annular ring 50. The slider 20 and base 30 are made of resin.

The tubular outer sheath 14 is passed through the inner sheath 12, which is also tubular, and the drive wire 13 is passed through the inner sheath 12. The inner sheath 12 is slidable within the outer sheath 14, and the drive wire 13 is slidable within the inner sheath 12.

The outer sheath 14 consists of a flexible hollow tube, and in this embodiment, a coil tube is used. As the coil tube, a flat wire coil tube consisting of a long flat plate made of metal (stainless steel) or the like, wound in a spiral shape can be used. However, a round wire coil tube or an inner flat coil tubes may also be used.

The inner sheath 12 consists of a flexible hollow tube, and in this embodiment, a wire tube is used. The wire tube is a tube made of hollow twisted wires, for example, a plurality of wires (cables) made of metal (stainless steel), and the like, twisted in a spiral shape so that they become hollow. As an example, experiments have shown that by using about 8 to 10 wires of 0.4 mm in diameter and twisting them so that the outer diameter is 1.5 to 1.7 mm and the inner diameter is 0.7 to 1 mm, a wire tube that can sufficiently withstand the compression force generated in the inner sheath during operation can be obtained. The wire tube obtained in the same way using a cable with a diameter of 0.3 mm was found to be insufficient to withstand the compressive force generated in the inner sheath during operation. The inner sheath 12 may be made primarily of a wire tube, with only a portion of the tip side of the inner sheath made of a coil tube.

The drive wire 13 consists of flexible wire, and in this embodiment, a wire rope is used. The wire rope is a rope consisting of a twisted wire made of a plurality of wires (cables) made of metal (stainless steel), for example, twisted into a spiral shape. However, a wire tube similar to the inner sheath 12 may be used as the drive wire 13.

The reason for using such a coil tube or wire tube made of twisted wires as the outer sheath 14 and inner sheath 12 is so that when this clip device 1 is ultrasonically cleaned with a cleaning solution, the cleaning solution can fully penetrate the inside of the tube and clean it well both inside and out.

It is preferable to use the winding direction of the outer sheath 14 and the winding direction of the inner sheath 12 opposite to each other in order to reduce the sliding resistance between them. For example, when the outer sheath 14 is wound Z, the inner sheath 12 is wound S. When a wire rope or wire tube made of twisted wires is used as the drive wire 13, it is likewise preferable to reverse the winding direction of the wire rope or wire tube to that of the inner sheath 12.

Figure 4:
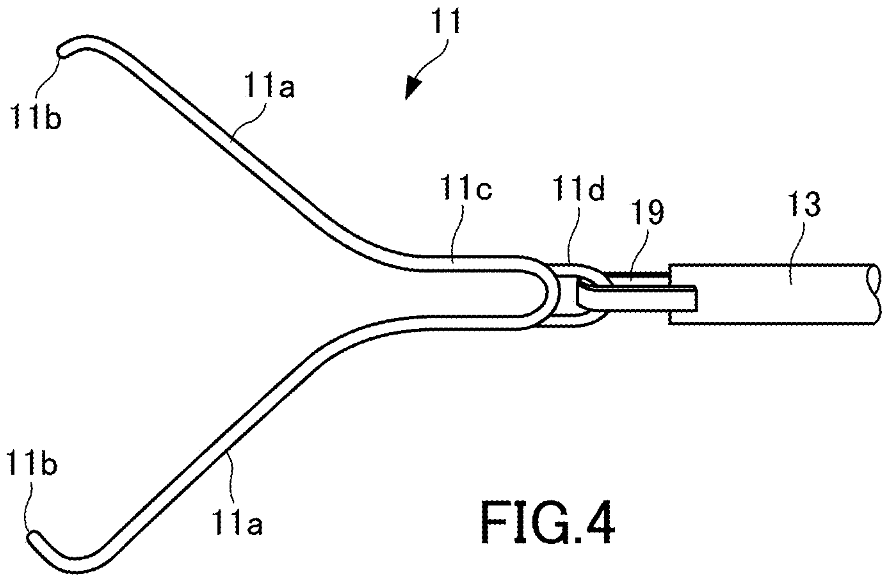
FIG. 4 shows a side view of a part of a connection hook and a drive wire that constitute the endoscopic treatment tool according to the first embodiment of the present invention.

The connection hook 11 in this embodiment has a pair of arm portions 11*a* made of elastic material arranged in a substantial V-shape toward its tip, as shown in FIG. 4. The connection hook 11 can take two states, open arm state (open state) and closed arm state (closed state), by cooperating with the inner sheath 12.

At the tip of each arm portion 11*a* of the connection hook 11, a claw portion 11*b* is formed respectively, which is bent inwardly to face each other. The connection hook 11 clips a connecting plate portion 42 of the clip body 41, which constitutes the clip 40 as the treatment component of the present invention to be described later, and each claw portion 11*b* engages, thereby connecting the clip 40 and the drive wire 13 in a detachable manner.

The connection hook 11 has a U-shaped portion 11*c* at its base end, which is formed in a substantial U-shape continuously with the base end of each arm portion 11*a*.

Each arm portion 11*a* including claw portion 11*b*, and U-shaped portion 11*c* are formed by suitably bending and plastically deforming one elongated plate material made of elastic material. Although not limited, the thickness of the plate material comprising the connection hook 11 is about 0.20 to 0.24 mm and the width is about 0.6 mm. The plate material is, for example, stainless steel.

A hook-side annular portion 11*d* is provided at the base of the U-shaped portion 11*c* of the connection hook 11. The hook-side annular portion 11*d* is integrally fixed to the connection hook 11 by fixing a pair of open ends of the U-shaped member to the outer surface of the base end of the U-shaped portion 11*c*, respectively. The hook-side annular portion 11*d* is fixed to the U-shaped portion 11*c* by means of laser welding or adhesion, for example.

As shown in FIG. 4, the distal end of the drive wire 13 (the left-hand end in FIG. 4) is provided with a wire-side annular portion 19. The wire-side annular portion 19 is integrally fixed to the drive wire 13 by a pair of open ends of a U-shaped member sandwiching the distal end of the drive wire 13 and joining the inner surface of the open ends with the side surface of the drive wire 13. The wire-side annular portion 19 is fixed to the drive wire 13 by means of laser welding or adhesion, for example.

As U-shaped members constituting the above hook-side annular portion 11*d* and wire-side annular portion 19, respectively, a plate material similar to the plate material constituting the connection hook 11, bent in an appropriate manner, can be used. For example, stainless steel can be used as the material of the U-shaped members constituting these annular portions 11*d*, 19, respectively. The semi-circular arc-shaped portions of these annular portions 11*d*, 19 have an outer diameter of about 1.0 to 1.2 mm and an inner diameter of about 0.8 to 1.0 mm, and their cross-sectional shapes, such as rectangular, circular or semi-circular shapes, are applicable.

The hook-side annular portion 11*d* and the wire-side annular portion 19 are chained to each other, so that the connection hook 11 is connected to the distal end of the drive wire 13 in a pivotable manner. By allowing the connection hook 11 to pivot about the distal end of the drive wire 13, rigidity of this portion within the inner sheath 12 is avoided, allowing the inner sheath 12 to pass smoothly over the curved portion of the endoscope passed through the digestive tract.

Figure 5A:
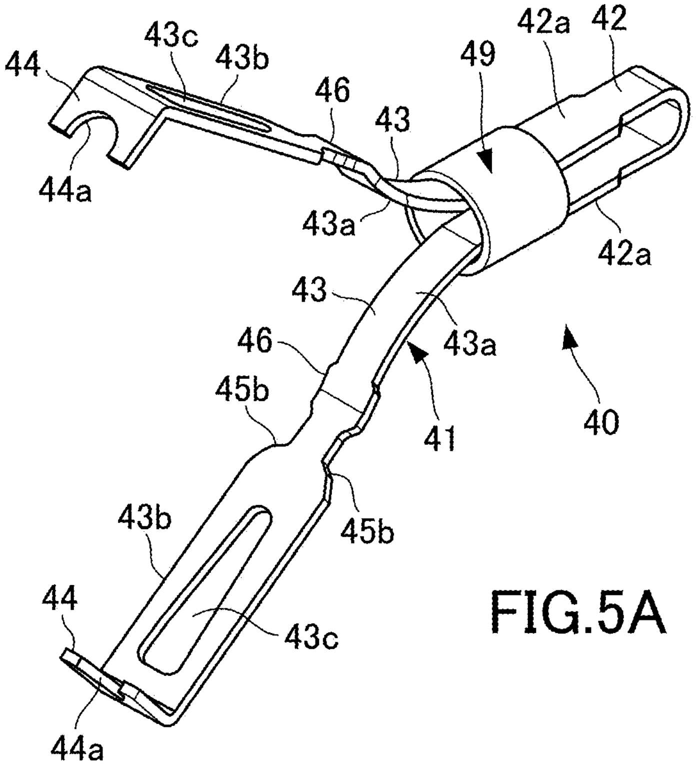
FIG. 5A shows a perspective view of a clip constituting the endoscopic treatment tool according to the first embodiment of the present invention, showing the clip in an open state.
Figure 5B:
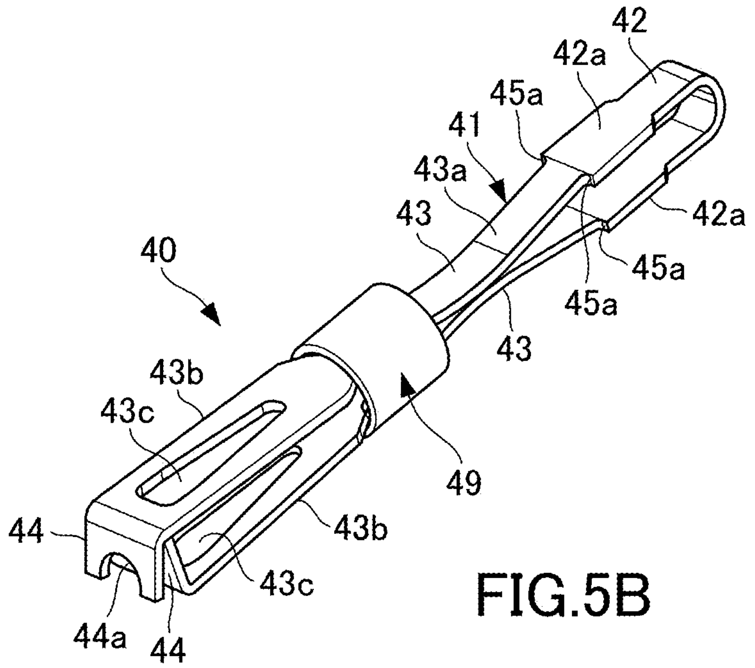
FIG. 5B shows a perspective view of the clip constituting the endoscopic treatment tool according to the first embodiment of the present invention, showing the clip in a closed state.

The clip device 1 according to the present embodiment is also equipped with a clip 40 shown in FIGS. 5A and 5B. The clip 40 is detachably held at the distal end of the drive wire 13 through the connection hook 11 and can be stored in the inner sheath 12 together with the connection hook 11.

As shown in FIGS. 5A and 5B, the clip 40 has a clip body 41 and a fastening ring 49. The fastening ring 49 is provided to be slidable with respect to an arm plate portion 43 to be described later of the clip body 41. The clip 40 is so configured that when the fastening ring 49 slides toward the proximal end, the clip body 41 is opened as shown in FIG. 5A, and when the fastening ring 49 moves toward the distal end, the clip body 41 is closed as shown in FIG. 5B.

The U-shaped connecting plate portion 42 has wide portions 42*a* at both ends of its distal end. The width of a base end portion 43*a* of each arm plate portion 43 is slightly smaller than the width of the wide portion 42*a* and a clipping portion 43*b* of the connecting plate portion 42. Due to this shape, as shown in FIG. 5B, a pair of fastening steps 45*a* are formed at the distal end edge of the wide portion 42*a* of the connecting plate portion 42 (on the base end portion 43*a* side of the arm plate portion 43) at both ends in the width direction thereof, respectively. As shown in FIG. 5A, at the end edge of the proximal end side of the clipping portion 43*b* (on the base end portion 43*a* side of the arm plate portion 43), a pair of fastening steps 45*b* are formed at both ends in the width direction, respectively. A through hole 43*c* is formed in the clipping portion 43*b* to reduce the weight of the clip body 41.

As shown in FIG. 5A, the base end portion 43*a* of each arm plate portion 43 has a ring fastening portion 46 formed with a larger width at the end on the clipping portion 43*b* side.

The fastening ring 49 is constituted by a substantially cylindrical member and is slidably attached to the base end portion 43*a* of each arm plate portion 43 of the clip body 41 along the direction in which the base end portion 43*a* extends. The fastening ring 49 may be constituted by a coil spring wound around a wire material in a coiled shape.

The fastening ring 49 is externally fitted to the base end portion 43*a* of the arm plate portion 43 so that the base end portion 43*a* of the arm plate portion 43 is passed through the inner space thereof and slides between the wide portion 42*a* of the connecting plate portion 42 and the clipping portion 43*b*.

As shown in FIG. 5A, when the fastening ring 49 is slid toward the proximal end, that is toward the connecting plate portion 42, the fastening ring 49 is stopped by contacting the respective fastening steps 45*a*, and further sliding toward the proximal end is restricted. At this time, the clip body 41 is in an open leg state with each arm plate portion 43 separated from each other by its own elasticity.

On the other hand, as shown in FIG. 5B, when the fastening ring 49 is slid toward the distal end, that is toward the clipping portion 43*b*, against the elasticity of each arm plate portion 43, the fastening ring 49 is stopped by contacting the respective stopping steps 45*b*, and further sliding toward the distal end is restricted. When the fastening ring 49 is slid toward the clipping portion 43*b*, each arm plate portion 43 is pressed closer toward each other by the fastening ring 49 and elastically deformed, and when the fastening ring 49 contacts each of the fastening steps 45*b*, the clip body 41 is completely closed. When the clip body 41 is closed in this manner, each of the claw portions 44 are superimposed on each other.

The clip 40 is configured such that when the fastening ring 49 contacts each of the fastening steps 45*b* and the clip body 41 is closed, each ring fastening portion 46 is press-fitted into the fastening ring 49. Each ring fastening portion 46 is thereby fastened by the fastening ring 49 to maintain the closed state of the clip body 41.

The clip 40 is connected to the connection hook 11 in the inner sheath 12 by having each claw portion 11*b* of the connection hook 11, which is closed, enter into the connecting plate portion 42 of the clip body 41. In this connected state within the inner sheath 12, when the connection hook 11 is pulled toward the proximal end of the clip 40, each claw portion 11*b* rides up on the connecting plate portion 42 to slightly open the arm 11*a*, allowing the connection hook 11 to detach from the clip 40 and disconnect from it.

Figure 6:
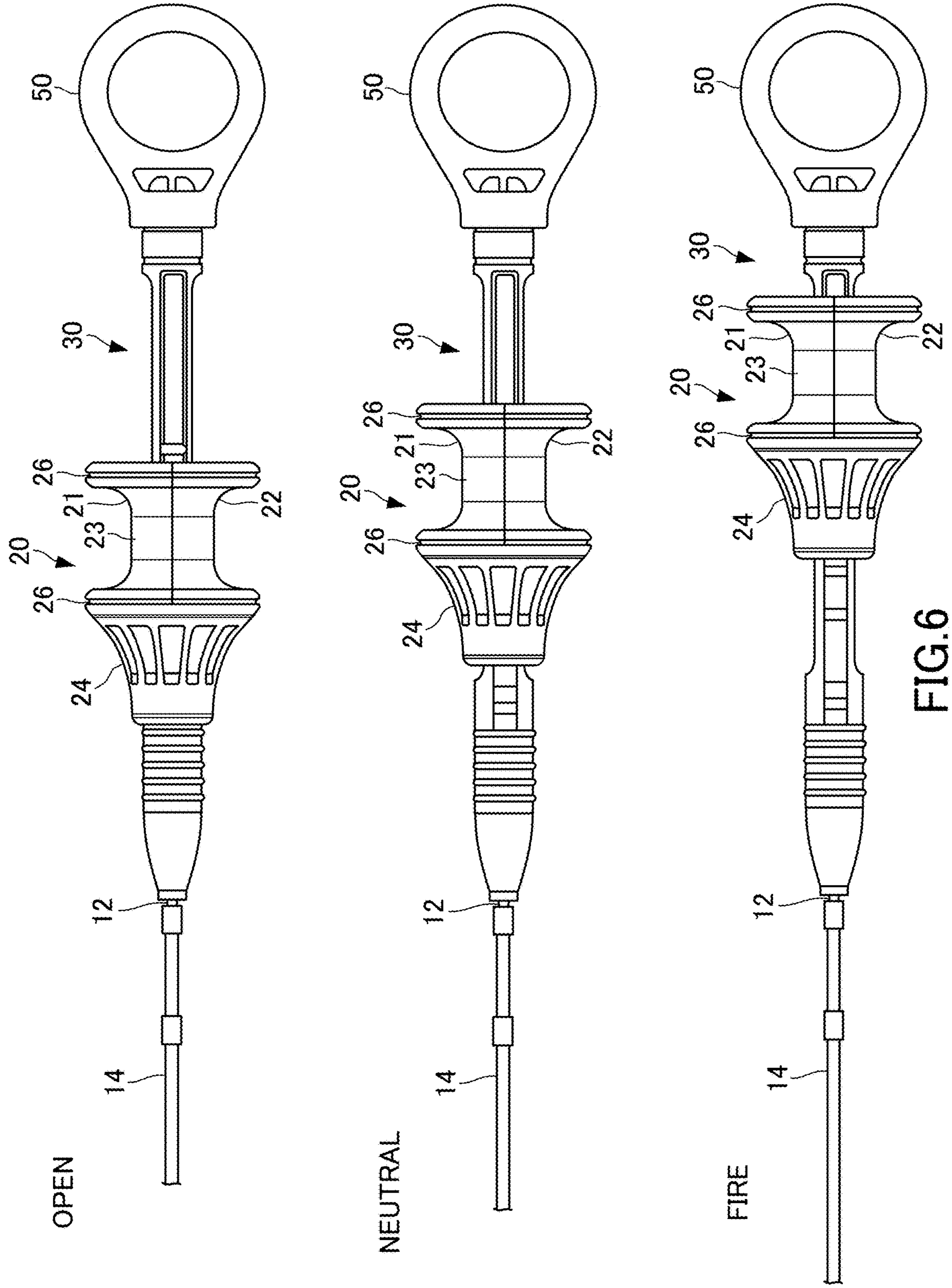
FIG. 6 shows a positional relationship between a slider and a base constituting the endoscopic treatment tool according to the first embodiment of the present invention, where the upper figure shows the positional relationship in an open position, the middle figure shows the positional relationship in a neutral position, and the lower figure shows the positional relationship in a fire position.
Figure 7:
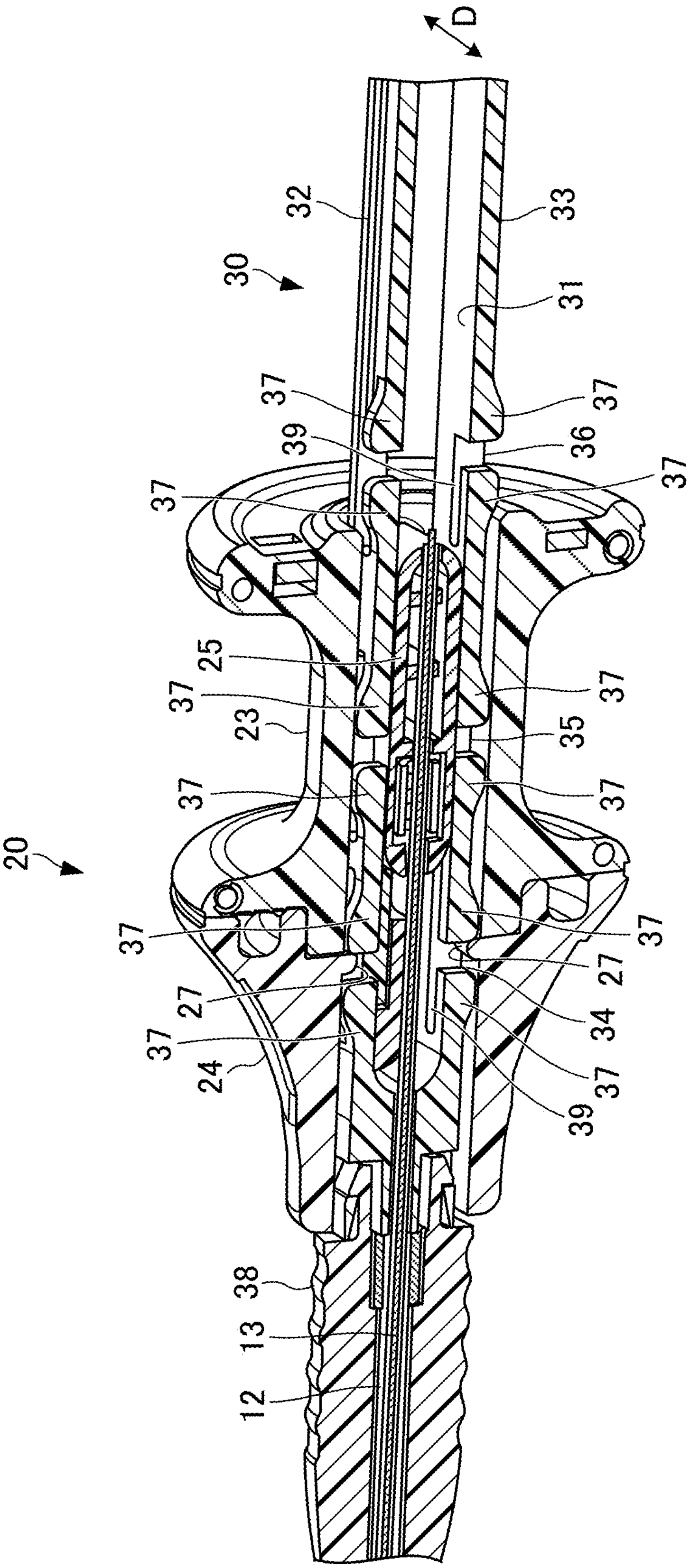
FIG. 7 shows a perspective cross-sectional view of the slider and the base constituting the endoscopic treatment tool according to the first embodiment of the present invention.

As shown in FIGS. 6 and 7, the slider 20 made of resin is slidably held against the base 30 in the axial direction of the inner sheath 12 and the drive wire 13. The slider 20 has a cylindrical body 23 comprising a pair of split cylindrical portions 21, 22 and a short cylindrical portion 24. The pair of split cylindrical portions 21, 22 face each other in the depth direction D of a guide groove 31 of the base 30 described below, and are mutually engaged at one end (proximal end side) in the axial direction, and are joined at the other end (distal end side) in the axial direction by the short cylindrical portion 24.

The slider 20 has a wire fixing portion 25 inside a cylindrical body 23 of a predetermined length surrounding the base 30, which is slidably guided into a guide groove 31 and to which the proximal end of the drive wire 13 is fixed. The proximal end of the drive wire 13 is integrally connected and fixed to the slider 20 by being sandwiched between the wire fixing portion 25 of the pair of split cylindrical portions 21, 22. In other words, the wire fixing portion 25 holding the proximal end of the drive wire 13 is constituted by the pair of split cylindrical portions 21, 22. Therefore, the drive wire 13 slides integrally when the slider 20 is slid in the axial direction.

The slider 20 has bridge portions 26 each protruding outwardly at both ends in the axial direction, and the portion between these bridge portions 26 can be held between, for example, an index finger and a middle finger. Here, when operating the slider by placing a finger in the space between the two bridge portions 26, the operator can easily operate the slider 20 without worrying about the orientation (position and posture) of the slider 20, since the slider 20 is configured in a substantially cylindrical shape.

In addition, inside the short cylindrical portion 24, when the slider 20 reaches one of a plurality of axial locations with respect to the base 30, a protruding portion 27 is formed as a concavo-convex engagement portion that concavo-convexly engages one of the plurality of positioning engagement portions 34, 35, 36 of the base 30 to be described below. The wire fixing portion 25 and the protruding portion 27 are formed at different positions from each other in the axial direction of the cylindrical body 23. The wire fixing portion 25 and the protruding portion 27 protrude inwardly in the radial direction of the cylindrical body 23 so as to cross each other.

When the protruding portion 27 engages one of the plurality of positioning engagement portions 34, 35, 36 of the base 30, the wire fixing portion 25 is slidably guided into the guide groove 31 of the base 30, avoiding the positioning engagement portion engaging the protruding portion 27 among the plurality of positioning engagement portions 34, 35, 36.

As shown in FIG. 7, the proximal end of the inner sheath 12 is connected via a sheath holder 38 to the approximate center of the tip of the base 30 made of resin.

As shown in FIG. 6, the annular ring 50 is supported at the base end of the base 30. The slider 20 can be easily slid against the base 30 with one hand by inserting the thumb into the annular ring 50 while holding the portion between the pair of bridge portions 26 of the slider 20 with the index and middle fingers.

The base 30 is held internally in the mating hole of the slider 20 so that the slider 20 can slide in the axial direction. The base 30 is always at least partially passed through the mating hole of the slider 20. The external shape of the base 30 and the internal shape of the mating hole of the slider 20 have a cross-sectional shape such as a perfect circle, ellipse or rectangle.

Figure 8A:
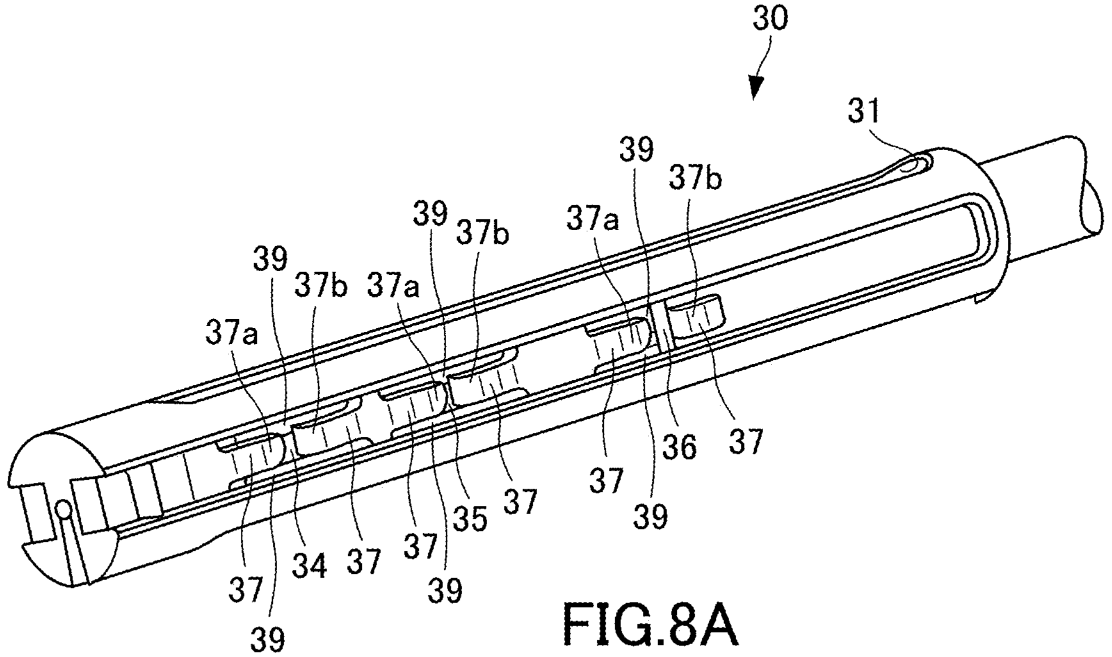
FIG. 8A shows a perspective view of the base constituting the endoscopic treatment tool according to the first embodiment of the present invention.
Figure 8B:
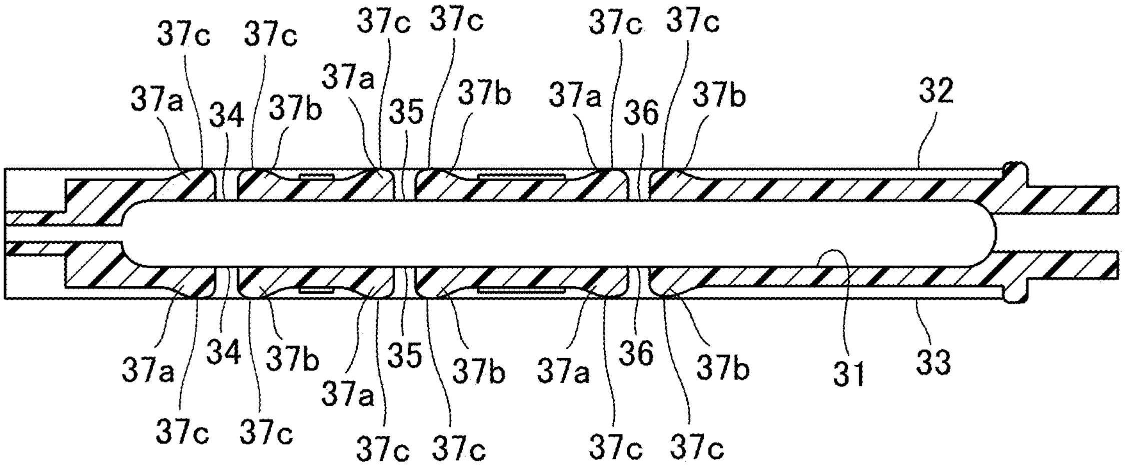
FIG. 8B shows a cross-sectional view of the base constituting the endoscopic treatment according to the first embodiment of the present invention.

As shown in FIGS. 7, 8A and 8B, the base 30 has a guide groove 31 extending in the axial direction. In both side walls 32, 33 of the guide groove 31, a plurality of positioning engagement portions 34, 35, 36 are formed in the form of holes at a plurality of locations differing from each other in the axial direction, which can be concavo-convexly engaged with the protruding portion 27 of the slider 20.

Furthermore, on at least one of the both side walls 32, 33, a spring portion 37 with cantilevered structure is integrally provided adjacent to the plurality of positioning engagement portions 34, 35, 36 by forming a groove 39 along the axial direction continuously with the plurality of positioning engagement portions 34, 35, 36. The spring portion 37 is designed to elastically engage the protruding portion 27 of the slider 20 with respect to each of the plurality of positioning engagement portions 34, 35, 36 in a concavo-convex manner.

The spring portion 37 is provided on both sides of each of the plurality of positioning engagement portions 34, 35, 36 in the axial direction. In other words, each positioning engagement portion 34, 35, 36 is formed by opposing free end portions 37*a*, 37*b* of a spring portion 37 on one side in the axial direction and a spring portion 37 on the other side in the axial direction.

The spring portion 37 on one side in the axial direction corresponding to each positioning engagement portion 34, 35, 36 and the spring portion 37 on the other side in the axial direction have a curved convex surface 37*c* protruding toward the inner wall of the mating hole of the cylindrical body 23 of the slider 20 on the respective free end portions 37*a*, 37*b* sides. This allows the spring portion 37 to smoothly bend when the protruding portion 27 of the slider 20 moves in contact with the curved convex surface 37*c* of the spring portion 37. On the other hand, when the protruding portion 27 of the slider 20 engages one of the plurality of positioning engagement portions 34, 35, 36, the spring portion 37 quickly returns to its original shape.

Thus, by providing a spring portion 37 with cantilevered structure in both side walls 32, 33 of the base 30, the sliding resistance when moving the slider 20 back and forth in the axial direction with respect to the base 30 can be made stronger or weaker (gentler or steeper). This allows the operator to clearly recognize the three positions (open position, neutral position, and fire position) required for device operation by the feeling of the slider 20 operation and the crackling sound when the protruding portion 27 of the slider 20 engages one of the plurality of positioning engagement portions 34, 35, 36.

As described above, the protruding portion 27 of the slider 20 engages with one of the positioning engagement portions 34, 35, 36 according to the sliding position of the slider 20 with respect to the base 30, so that the slider 20 can be positioned with respect to the base 30 in three positions (open position, neutral position and fire position).

Figure 9:
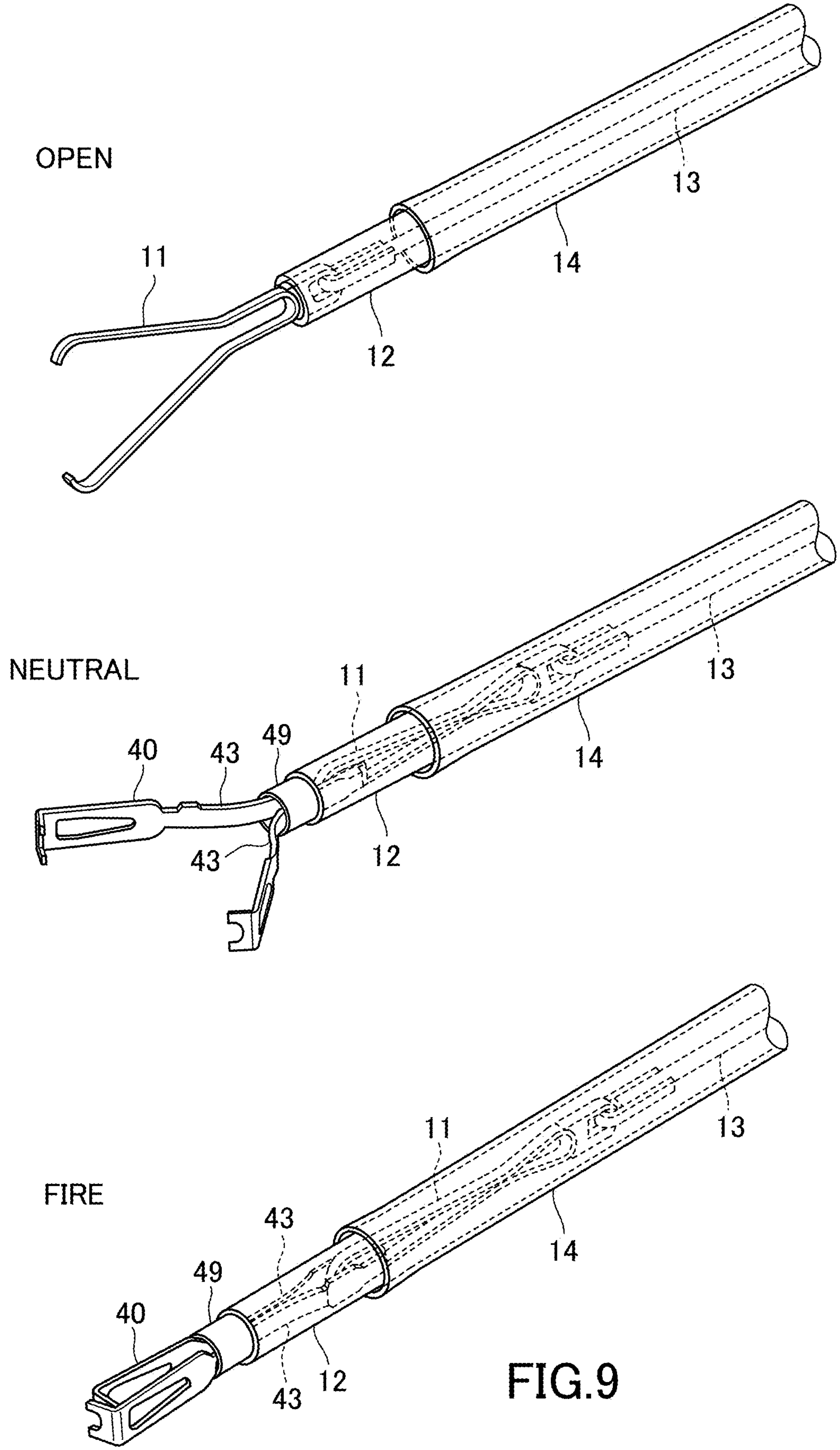
FIG. 9 shows a perspective view illustrating the action of the connection hook and the clip constituting the endoscopic treatment tool according to the first embodiment of the present invention, where the upper figure shows the connection hook in an open state in the open position, the middle figure shows the clip in a closed state in the neutral position, and the lower figure shows the clip in a closed state in the closed position.
Figure 10:
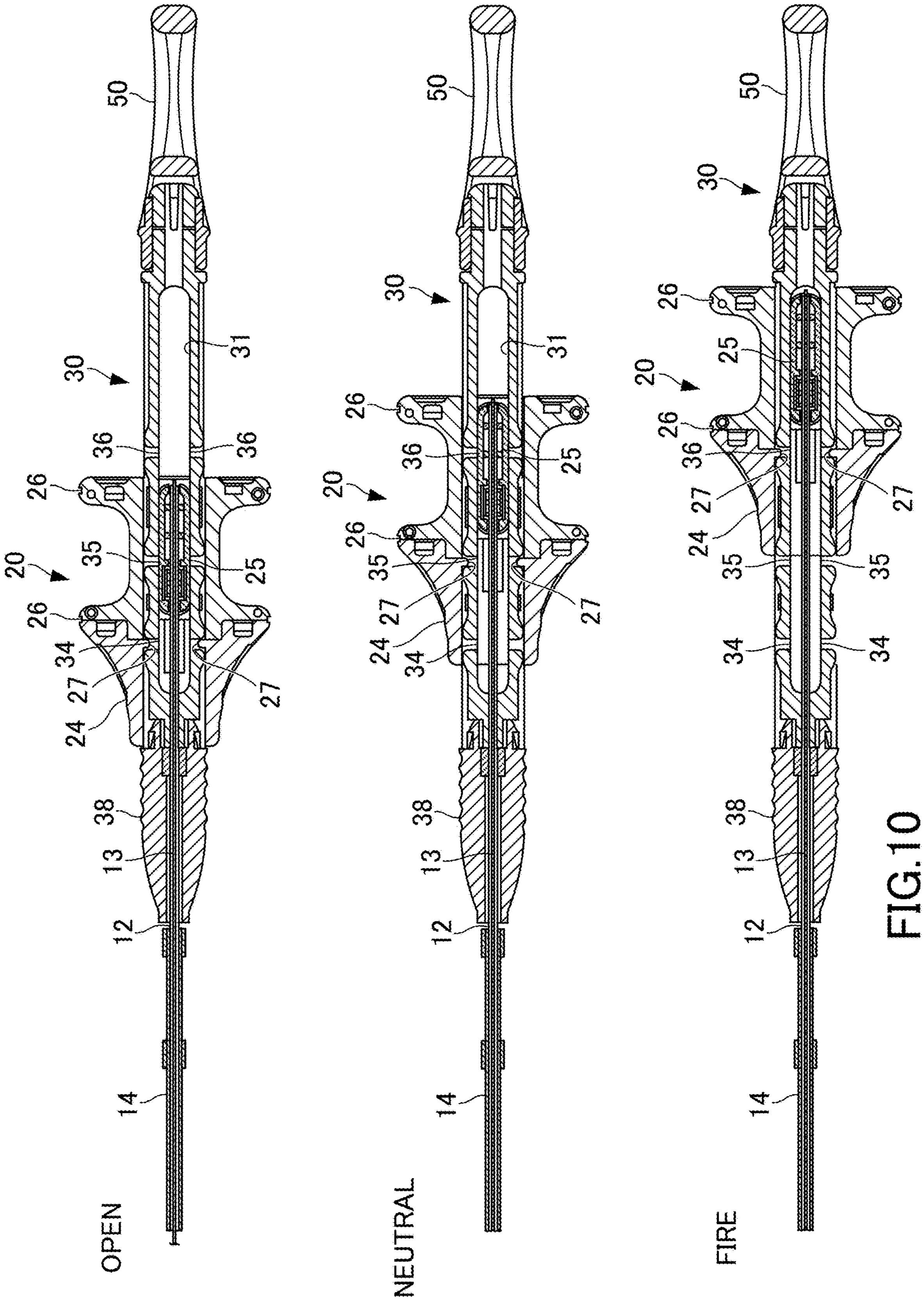
FIG. 10 shows the change in an engagement position between a protruding portion of the slider and a positioning engagement portion of the base, which constitute the endoscopic treatment tool according to the first embodiment of the present invention, where the upper figure shows the engagement position in the open position, the middle figure shows the engagement position in the neutral position, and the lower figure shows the engagement position in the fire position.
Figure 11A:
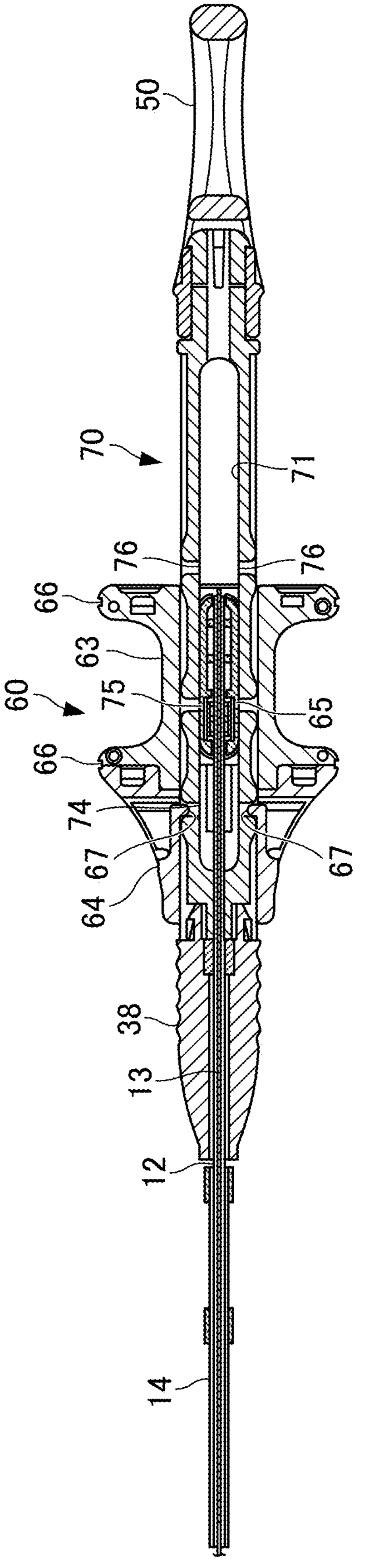
FIG. 11A shows a cross-sectional view of the endoscopic treatment tool according to the second embodiment of the present invention, showing the II-II cross-sectional view of FIG. 1.
Figure 11B:
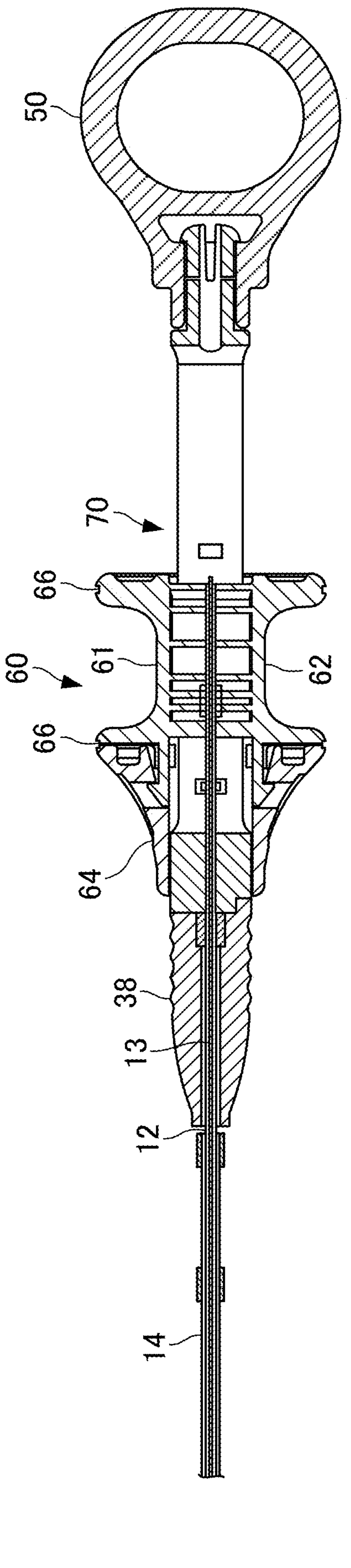
FIG. 11B shows a cross-sectional view of the endoscopic treatment tool according to the second embodiment of the present invention, perpendicular to the II-II cross-section of FIG. 1.

As shown in the upper rows of FIGS. 9 and 10, respectively, the open position is the position in which the connection hook 11 is opened (open arms) and the slider 20 is pulled out the most from the base 30. In the open position, the protruding portion 27 of the slider 20 elastically engages the positioning engagement portion 34 of the base 30 to hold it in place.

As shown in the lower rows of FIGS. 9 and 10, respectively, the fire position is the position where the fastening ring 49 is slid onto the clip 40 clipped by the connection hook 11 for fastening operation, and where the slider 20 is pushed in the most against the base 30. In the fire position, the protruding portion 27 of the slider 20 elastically engages the positioning engagement portion 36 of the base 30 to hold it in place.

As shown in the middle rows of FIGS. 9 and 10, respectively, the neutral position is the position where the clip 40 is connected (clipped) by closing the connection hook 11 without any fastening action on the clip 40, and is the position set between the open position and the fire position. In the neutral position, the protruding portion 27 of the slider 20 elastically engages the positioning engagement portion 35 of the base 30 to hold it in place.

Next, the operation of the clip device 1 will be described with reference to FIGS. 9 and 10. First, the right thumb, for example, is passed through the annular ring 50, and the portions between the pair of bridge portions 26 of the slider 20 are held between the index and middle fingers of the right hand, for example, and are manipulated to separate from each other to set the slider 20 in the most withdrawn position from the base 30. This position is the open position described above. Although the description here is mainly for one-handed operation, it may of course be operated with both hands, for example, by grasping the slider 20 or a nearby part thereof with the left hand and the annular ring 50 or a nearby part thereof with the right hand.

In the open position, the protruding portion 27 of the slider 20 is elastically engaged with the positioning engagement portion 34 of the base 30 and is held in that state. In this state, a portion of the distal end of the short cylindrical portion 24 of the slider 20 contacts a portion of the proximal end of the sheath holder 38, thereby restricting further sliding (withdrawal) of the slider 20 against the base 30.

By this operation, the connection hook 11 connected to the distal end of the drive wire 13 is pushed out of the inner sheath 12 and protrudes from the tip of the inner sheath 12, opening its arms in a substantial V-shape by its own elasticity.

Next, the connection hook 11 at the tip of the sheath of the clip device 1 is positioned so that the connecting plate portion 42 of the clip 40 to be connected to it can be grasped.

In this state, when the right thumb, for example, is passed through the annular ring 50, and while holding the portion between the pair of bridge portions 26 of the slider 20, for example, with the index and middle fingers of the right hand, the slider 20 is operated so that they are close to each other, the slider 20 is slid toward the base 30 in the retracting direction, and the slide is stopped at the neutral position. In the neutral position, the protruding portion 27 of the slider 20 elastically engages the positioning engagement portion 35 of the base 30 to hold it in place.

By this operation, the drive wire 13 is pulled into the inner sheath 12, the connection hook 11 connected to the distal end of the drive wire 13 is embedded in the tip of the inner sheath 12 and closed, and the clip 40 is connected to the tip of the sheath of the clip device 1. In this state, the fastening ring 49 of the clip 40 is not slid, and the pair of arm plate portions 43 of the clip 40 are in an open state due to their own elasticity.

Next, the outer sheath 14 is pushed out against the inner sheath 12 and the drive wire 13, and the connection hook 11 to which the clip 40 is connected and the clip 40 are embedded in the outer sheath 14, and is accommodated in the tip of the outer sheath 14 with the clip 40 in a closed state. In this state, the fastening ring 49 of the clip 40 remains in the previous position, and the fastening operation of the clip 40 is not performed.

In this state, the clip device 1 is passed through the treatment tool guide tube of the endoscope (not shown) and introduced to the affected part where clipping of the clip 40 should stop bleeding or the like. Once the tip of the outer sheath 14 has reached the affected part, the outer sheath 14 is retracted against the inner sheath 12, and the clip 40 connected to the connection hook 11 protrudes from the tip of the outer sheath 14 and is returned to the open state by its own elasticity.

Once the clip 40 has been introduced into the appropriate position in the patient's body cavity and its posture adjusted, etc., the slider 20 is retracted to the hand side position of the base 30 and slid to the most retracted position (the most hand side position). This position is the fire position described above.

In the fire position, the protruding portion 27 is elastically engaged with the positioning engagement portion 36 of the base 30 to hold it in place. In this state, a portion of the portion of the base 30 to which the annular ring 50 is attached is in contact with a portion of the distal end side of the slider 20, thereby restricting further sliding of the slider 20 with respect to the base 30.

This causes the drive wire 13 to be retracted further into the inner sheath 12, that is, the connection hook 11 is retracted further into the inner sheath 12, the fastening ring 49 of the clip 40 is pushed out by the tip of the inner sheath 12 and slid into the fastening position, the clip 40 clips the affected part, so that the clip 40 is then closed and fixed with the clip 40 clipping the affected part.

When clipping of the clip 40 to the affected part is completed, the slider 20 is slid to the open position, which is the position at the leading edge of the base 30, and the clipping of the clip 40 by the connection hook 11 is released to complete the series of operations.

As explained above, the clip device 1 of this embodiment has a spring portion 37 with cantilever structure integrally provided on the base 30, so that the spring portion 37 with cantilever structure can be integrally formed by resin or the like. Therefore, the elastic concavo-convex engagement state of the plurality of positioning engagement portions 34, 35, 36 of the base 30 and the protruding portion 27 of the slider 20 via this spring portion 37 with cantilevered structure and the corresponding strength (gentle or steep) of the operating resistance of the slider 20 can be easily and accurately set according to changes in the slide position. Therefore, the operation feeling of the slider 20 against the base 30 and the corresponding operation sound can be clarified, and the operation of the slider 20 related to the attachment and detachment of the clip 40 by the connection hook 11 can be facilitated and its operation position can be clarified. In addition, compared to conventional products that use a plurality of plate springs, and the like, in separate pieces, the structure can be downsized and simplified by reducing the number of parts, and the number of assembly man-hours can be reduced, thereby enabling reduction in manufacturing costs.

In addition, the clip device 1 of this embodiment, when the spring portion 37 with cantilever structure bends to engage the protruding portion 27 of the slider 20 with one of the plurality of positioning engagement portions 34, 35, 36 of the base 30, the positioning engagement portion that engages the protruding portion 27 of the plurality of positioning engagement portions 34, 35, 36 is avoided, and the wire fixing portion 25 of the slider 20 is slidably guided In other words, the positions of the protruding portion 27 and the wire fixing portion 25 are set so that the slider 20 can slide against the base 30 while considering the flexure of the spring portion 37. Therefore, even if the flexure range of the spring portion 37 with cantilever structure is set to the inner side in the radial direction, the flexure of the spring portion 37 with cantilever structure does not impair the guiding function of the slider 20, and together with the simplification of the structure, the device diameter can be reduced.

In addition, the clip device 1 of this embodiment can easily arrange an operation cam surface on the outer side of the spring portion 37 with cantilevered structure that forms the guide groove 31 on the inner side, which provides operation resistance according to the slide position of the slider 20 and clarifies the operation position.

In addition, the clip device 1 of the present embodiment can set the flexure range of the spring portion 37 with cantilever structure to the inner side in the radial direction, so that it is possible to reduce the diameter of the device.

In the clip device 1 of the present embodiment, each positioning engagement portion 34, 35, 36 of the base 30 is formed by the opposing free end portions 37*a*, 37*b* of the spring portion 37 with cantilevered structure on both sides in the axial direction. For this reason, it is possible to precisely set the operating resistance of the spring portion 37 with cantilevered structure in accordance with the sliding position of the slider 20, so that it is possible to obtain a good operation feeling and operation sound.

Further, in the clip device 1 of the present embodiment, since the spring portions 37 with cantilevered structure on both sides in the axial direction corresponding to the plurality of positioning engagement portions 34, 35, 36 of the base 30 have curved convex surfaces 37*c* protruding toward the inner wall of the mating hole of the cylindrical body 23 of the slider 20 on the respective free end portions 37*a*, 37*b* sides, the guiding function of the cylindrical body 23 of the slider 20 can be stabilized and the operation feeling can be improved.

In addition, the clip device 1 of the present embodiment allows the cylindrical body 23 to be made of resin molding, and also facilitates the fixing work of the drive wire 13.

Second Embodiment

The clip device according to the second embodiment of the invention will be described with reference to the drawings. The same symbols will be used for the same configuration as in the first embodiment, and the description will be omitted as appropriate. The description of the same operations as in the first embodiment will also be omitted as appropriate.

As shown in FIGS. 1, 2, 11A, and 11B, the clip device 2 according to the second embodiment of the present invention is generally composed of the connection hook 11, the inner sheath 12, the drive wire 13, the outer sheath 14, a slider 60, a base 70, and the annular ring 50. The slider 60 and base 70 are made of resin.

The slider 60, which is made of resin, is slidably held against the base 70 in the axial direction of the inner sheath 12 and the drive wire 13. The slider 60 has a cylindrical body 63 comprising a pair of split cylindrical portions 61, 62 and a short cylindrical portion 64. The pair of split cylindrical portions 61,62 face each other in the depth direction D (see FIG. 12) of the guide groove 71 of the base 70, which is described below, and are mutually engaged at one end (proximal end side) in the axial direction and joined at the other end (distal end side) in the axial direction by the short cylindrical portion 64.

The slider 60 has a wire fixing portion 65 inside a cylindrical body 63 of a predetermined length surrounding the base 70, which is slidably guided into a guide groove 71 and to which the proximal end of the drive wire 13 is fixed. The proximal end of the drive wire 13 is integrally connected and fixed to the slider 60 by being sandwiched between the wire fixing portion 65 of the pair of split cylindrical portions 61, 62. In other words, the wire fixing portion 65 holding the proximal end of the drive wire 13 is composed of the pair of split cylindrical portions 61, 62. Therefore, the drive wire 13 is slid integrally when the slider 60 is slid in the axial direction.

The slider 60 has bridge portions 66 each protruding outwardly at both ends in the axial direction, and the portion between these bridge portions 66 can be held between, for example, an index finger and a middle finger. Here, when operating the slider by placing a finger in the space between the two bridge portions 66, the operator can easily operate the slider 60 without worrying about the orientation (position and posture) of the slider 60, since the slider 60 is configured in a substantially cylindrical shape.

Figure 12:
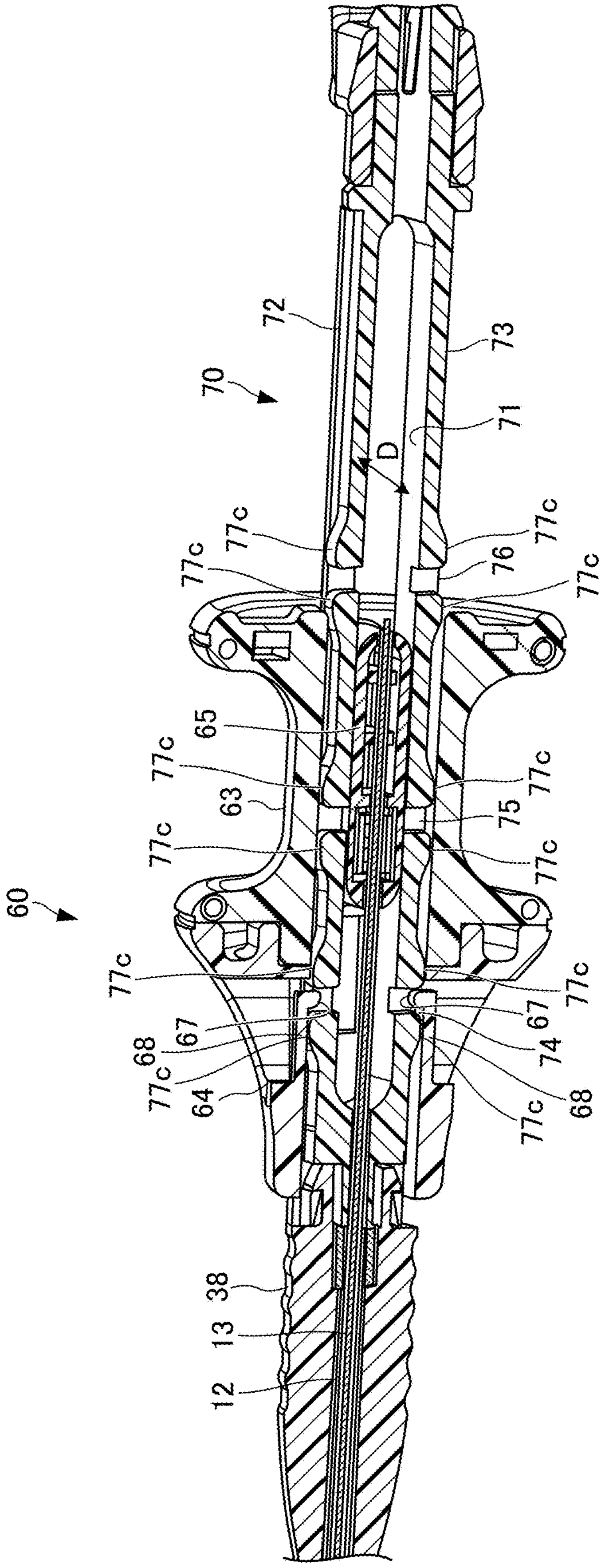
FIG. 12 shows a cross-sectional view of a slider and a base constituting the endoscopic treatment tool according to the second embodiment of the present invention.
Figure 13A:
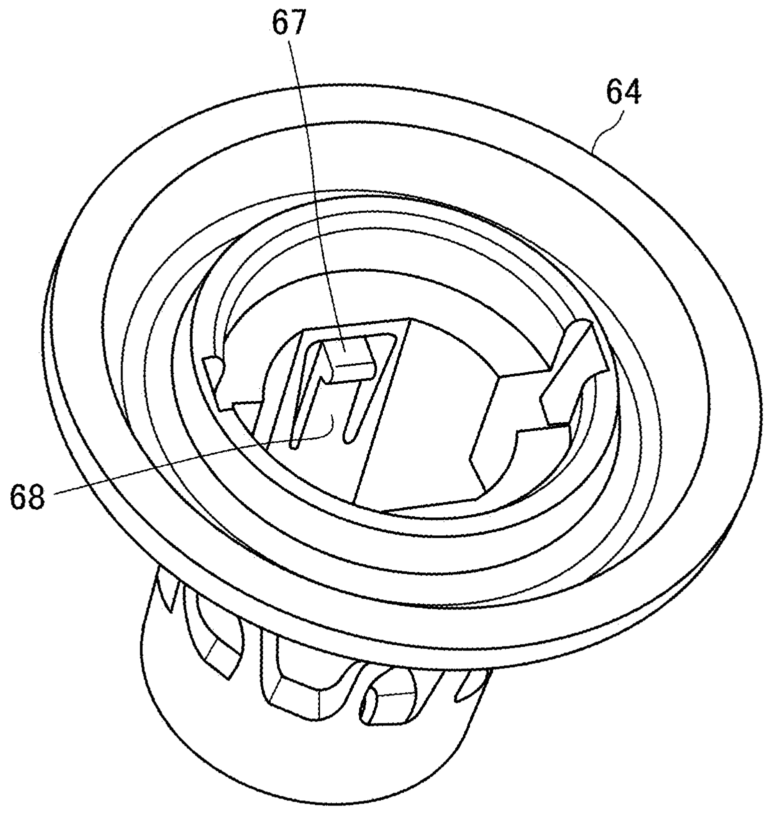
FIG. 13A shows a perspective view of a short cylindrical part of the slider constituting the endoscopic treatment tool according to the second embodiment of the present invention.
Figure 13B:
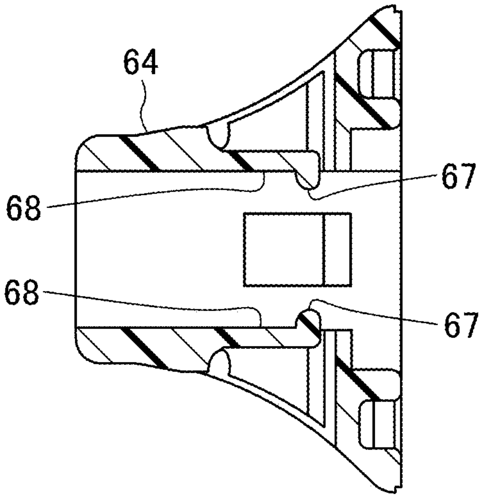
FIG. 13B shows a cross-sectional view of the short cylindrical part of the slider constituting the endoscopic treatment tool according to the second embodiment of the present invention.

As shown in FIGS. 12, 13A, and 13B, inside the short cylindrical portion 64, when the slider 60 reaches one of a plurality of axial locations relative to the base 70, a protruding portion 67 as a concavo-convex engagement portion that concavo-convexly engages one of the plurality of positioning engagement portions 74, 75, 76 of the base 70 to described below. The wire fixing portion 65 and the protruding portion 67 are formed at different positions from each other in the axial direction of the cylindrical body 63. The wire fixing portion 65 and the protruding portion 67 protrude inwardly in the radial direction of the cylindrical body 63 so as to cross each other.

When the protruding portion 67 engages one of the plurality of positioning engagement portions 74, 75, 76 of the base 70, the wire fixing portion 65 is slidably guided into the guide groove 71 of the base 70, avoiding the positioning engagement portion engaging the protruding portion 67 among the plurality of positioning engagement portions 74, 75, 76.

Further, in the slider 60, a spring portion 68 with cantilevered structure is provided adjacent to the protruding portion 67. The spring portion 68 is designed to elastically engage the protruding portion 67 of the slider 60 with respect to each of the plurality of positioning engagement portions 74, 75, 76 in a concavo-convex manner.

As shown in FIG. 12, the proximal end of the inner sheath 12 is connected via the sheath holder 38 to the approximate center of the tip of the base 70 made of resin.

The annular ring 50 is supported at the base end of the base 70. The slider 60 can be easily slid against the base 70 with one hand by inserting the thumb into the annular ring 50 while holding the portion between the pair of bridge portions 66 of the slider 60 with the index and middle fingers.

The base 70 is held internally in the mating hole of the slider 60 so that the slider 60 can slide in the axial direction. The base 70 is always at least partially passed through the mating hole of the slider 60. The external shape of the base 70 and the internal shape of the mating hole of the slider 60 have a cross-sectional shape such as a perfect circle, ellipse or rectangle.

As shown in FIG. 12, the base 70 has a guide groove 71 extending in the axial direction. In both side walls 72, 73 of the guide groove 71, a plurality of positioning engagement portions 74, 75, 76 are formed in the form of holes at a plurality of locations differing from each other in the axial direction, which can be concavo-convexly engaged with the protruding portion 67 of the slider 60.

On both sides in the axial direction of each of the positioning engagement portions 74, 75, 76, curved convex surfaces 77*c* are formed protruding toward the inner wall surface of the mating hole of the cylindrical body 63 of the slider 60. This allows the spring portion 68 of the slider 60 to smoothly bend when the protruding portion 67 of the slider 60 moves in contact with the curved convex surface 77*c* of the base 70. On the other hand, when the protruding portion 67 of the slider 60 engages one of the plurality of positioning engagement portions 74, 75, 76, the spring portion 68 quickly returns to its original shape.

Similar to the base 30 in the first embodiment, a spring portion with cantilevered structure may be provided on both sides of each positioning engagement portion 74, 75, 76 of the base 70 in the axial direction.

Thus, by providing a spring portion 68 with cantilevered structure in the slider 60, the sliding resistance when moving the slider 60 back and forth in the axial direction with respect to the base 70 can be made stronger or weaker (gentler or steeper). This allows the operator to clearly recognize the three positions (open position, neutral position, and fire position) required for device operation by the feeling of the slider 60 operation and the crackling sound when the protruding portion 67 of the slider 60 engages one of the plurality of positioning engagement portions 74, 75, 76.

As described above, the protruding portion 67 of the slider 60 engages with one of the positioning engagement portions 74, 75, 76 according to the sliding position of the slider 60 with respect to the base 70, so that the slider 60 can be positioned with respect to the base 70 in three positions (open position, neutral position and fire position).

Figure 14:
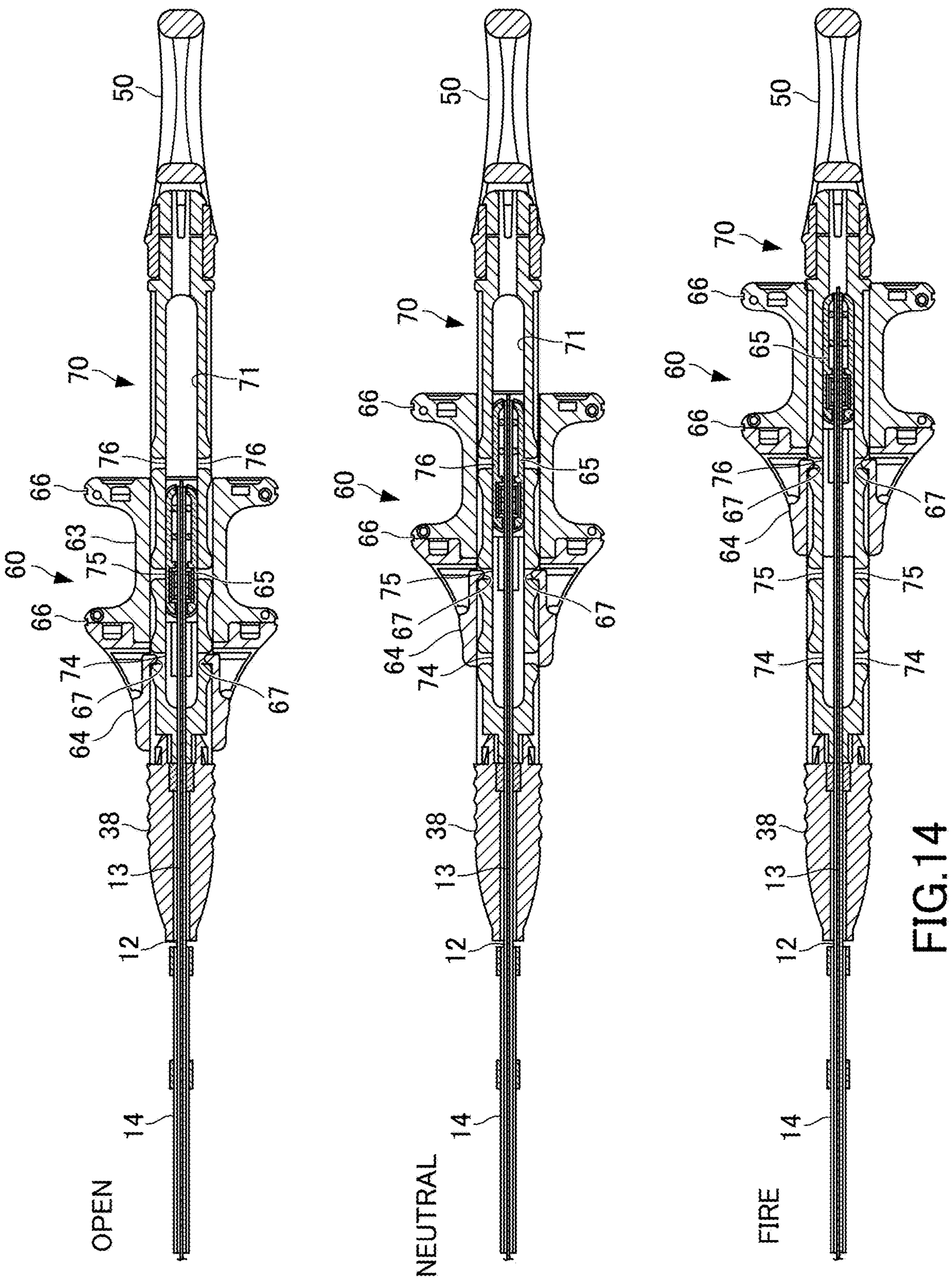
FIG. 14 shows the change in an engagement position between a protruding portion of the slider and a positioning engagement portion of the base, which constitutes the endoscopic treatment tool according to the second embodiment of the present invention, where the upper figure shows the engagement position in the open position, the middle figure shows the engagement position in the neutral position, and the lower figure shows the engagement position in the fire position.

As shown in the upper rows of FIGS. 9 and 14, respectively, the open position is the position in which the connection hook 11 is opened (open arms) and the slider 60 is pulled out the most from the base 70. In the open position, the protruding portion 67 of the slider 60 elastically engages the positioning engagement portion 74 of the base 70 to hold it in place.

As shown in the lower rows of FIGS. 9 and 14, respectively, the fire position is the position where the fastening ring 49 is slid to the clip 40 clipped by the connection hook 11 for fastening operation, and where the slider 60 is pushed in most against the base 70. In the fire position, the protruding portion 67 of the slider 60 elastically engages the positioning engagement portion 76 of the base 70 to keep its position.

As shown in the middle rows of FIGS. 9 and 14, respectively, the neutral position is the position where the clip 40 is connected (clipped) by closing the connection hook 11 without any fastening action on the clip 40, and is the position set between the open position and the fire position. In the neutral position, the protruding portion 67 of the slider 60 elastically engages the positioning engagement portion 75 of the base 70 to hold it in place.

Next, the operation of the clip device 2 will be described with reference to FIGS. 9 and 14. First, the right thumb, for example, is passed through the annular ring 50, and the portions between the pair of bridge portions 66 of the slider 60 are held between the index and middle fingers of the right hand, for example, and are manipulated to separate from each other to set the slider 60 in the most withdrawn position from the base 70. This position is the open position described above. Although the description here is mainly for one-handed operation, it may of course be operated with both hands, for example, by grasping the slider 60 or a nearby part thereof with the left hand and the annular ring 50 or a nearby part thereof with the right hand.

In the open position, the protruding portion 67 of the slider 60 is elastically engaged with the positioning engagement portion 74 of the base 70 and is held in that state. In this state, a portion of the distal end of the short cylindrical portion 64 of the slider 60 contacts a portion of the proximal end of the sheath holder 38, thereby restricting further sliding (withdrawal) of the slider 60 against the base 70.

By this operation, the connection hook 11 connected to the distal end of the drive wire 13 is pushed out of the inner sheath 12 and protrudes from the tip of the inner sheath 12, to open its arms in a substantial V-shape by its own elasticity.

Next, the connection hook 11 at the end of the sheath of the clip device 2 is positioned so that the connecting plate portion 42 of the clip 40 to be connected to it can be grasped.

In this state, when the right thumb, for example, is passed through the annular ring 50, and while holding the portion between the pair of bridge portions 66 of the slider 60, for example, with the index and middle fingers of the right hand, the slider 60 is operated so that they are close to each other, the slider 20 is slid toward the base 30 in the retracting direction, and the slide is stopped at the neutral position. In the neutral position, the protruding portion 67 of the slider 60 elastically engages the positioning engagement portion 75 of the base 70 to hold it in place.

By this operation, the drive wire 13 is pulled into the inner sheath 12, the connection hook 11 connected to the distal end of the drive wire 13 is embedded in the tip of the inner sheath 12 and closed, and the clip 40 is connected to the tip of the sheath of the clip device 2. In this state, the fastening ring 49 of the clip 40 is not slid, and the pair of arm plate portions 43 of the clip 40 are in an open state due to their own elasticity.

Next, the outer sheath 14 is pushed out against the inner sheath 12 and the drive wire 13, and the connection hook 11 to which the clip 40 is connected and the clip 40 are embedded in the outer sheath 14, and is accommodated in the tip of the outer sheath 14 with the clip 40 in a closed state. In this state, the fastening ring 49 of the clip 40 remains in the previous position, and the fastening operation of the clip 40 is not performed.

In this state, the clip device 2 is passed through the treatment tool guide tube of the endoscope (not shown) and introduced to the affected part where clipping of the clip 40 should stop bleeding, and the like. Once the tip of the outer sheath 14 has reached the affected part, the outer sheath 14 is retracted against the inner sheath 12, and the clip 40 connected to the connection hook 11 protrudes from the tip of the outer sheath 14 and is returned to the open leg state by its own elasticity.

Once the clip 40 has been introduced into the appropriate position in the patient's body cavity and its posture adjusted, etc., the slider 60 is retracted to the hand side position of the base 70 and slid to the most retracted position (the most hand side position). This position is the fire position described above.

In the fire position, the protruding portion 67 is elastically engaged with the positioning engagement portion 76 of the base 70 to hold it in place. In this state, a portion of the portion of the base 70 to which the annular ring 50 is attached is in contact with a portion of the distal end side of the slider 60, thereby restricting further sliding of the slider 60 with respect to the base 70.

This causes the drive wire 13 to be retracted further into the inner sheath 12, that is, the connection hook 11 is retracted further into the inner sheath 12, the fastening ring 49 of the clip 40 is pushed out by the tip of the inner sheath 12 and slid into the fastening position, the clip 40 clips the affected part, so that the clip 40 is then closed and fixed with the clip 40 clipping the affected part.

When clipping of the clip 40 to the affected part is completed, the slider 60 is slid to the open position, which is the position at the leading edge of the base 70, and the clipping of the clip 40 by the connection hook 11 is released to complete the series of operations.

As explained above, the clip device 2 of this embodiment provides the spring portion 68 with cantilever structure integrally in the slider 60, so that the spring portion 68 with cantilever structure can be formed integrally by resin or the like. Therefore, the elastic concavo-convex engagement state of the plurality of positioning engagement portions 74, 75, 76 of the base 70 and the protruding portion 67 of the slider 60 via the spring portion 68 with cantilevered structure and the corresponding strength (gentle or steep) of the operating resistance of the slider 60 can be easily and accurately set according to changes in the slide position. Therefore, the operation feeling of the slider 60 against the base 70 and the corresponding operation sound can be clarified, and the operation of the slider 60 related to the attachment and detachment of the clip 40 by the connection hook 11 can be facilitated and its operation position can be clarified. In addition, compared to conventional products that use a plurality of plate springs, and the like, in separate pieces, the structure can be downsized and simplified by reducing the number of parts, and the number of assembly man-hours can be reduced, enabling reduction in manufacturing costs.

In addition, the clip device 2 of this embodiment, when the spring portion 68 with cantilevered structure bends to engage the protruding portion 67 of the slider 60 with one of the plurality of positioning engagement portions 74, 75, 76 of the base 70, the positioning engagement portion that engages the protruding portion 67 of the plurality of positioning engagement portions 74, 75, 76 is avoided, and the wire fixing portion 65 of the slider 60 is slidably guided. In other words, the positions of the protruding portion 67 and the wire fixing portion 65 are set so that the slider 60 can slide against the base 70 while considering the flexure of the spring portion 68. Therefore, even if the flexure range of the spring portion 68 with cantilever structure is set to the inner side in the radial direction, the flexure of the spring portion 68 with cantilever structure does not impair the guiding function of the slider 60, and together with the simplification of the structure, the device diameter can be reduced.

The clip device 2 of this embodiment has curved convex surfaces 77*c* protruding toward the inner wall of the mating hole of the cylindrical body 63 of the slider 60 on both sides in the axial direction of the plurality of positioning engagement portions 74, 75, 76 of the base 70, which can stabilize the guiding function of the cylindrical body 63 of the slider 60 and can improve the operation feeling.

Since the clip device 2 of the present embodiment has a spring portion 68 with cantilevered structure in the slider 60, the length of the spring portion 68 can be set more freely, thereby making the operation feeling of the slider 60 better. In addition, it is no longer necessary to provide the spring portion on the base 70 side, so that the degree of freedom of its shape can be increased.

In addition, the clip device 2 of the present embodiment allows the cylindrical body 63 to be made of resin molding and also facilitates the fixing work of the drive wire 13.

EXPLANATION OF REFERENCE NUMERALS

1, 2 Clip Device (Endoscopic Treatment Tool)
11 Connection Hook
12 Inner Sheath (Sheath)
13 Drive Wire
14 Outer Sheath
20, 60 Slider
21, 22, 61, 62 Split Cylindrical Portion
23, 63 Cylindrical Body
24, 64 Short Cylindrical Portion
25, 65 Wire Fixing Portion
27, 67 Protrusion Portion (Concavo-Convex Engagement Portion)
30, 70 Base
31, 71 Guide Groove
32, 33, 72, 73 Both Side Walls
34, 35, 36, 74, 75, 76 Positioning Engagement Portion
37, 68 Spring Portion
37*a*, 37*b* Free End Portion
37*c*, 77*c* Curved Convex Surface
40 Clip (Treatment Component)
50 Annular Ring
D Depth Direction

What is claimed is:

1. An endoscopic treatment tool, comprising:

a tubular sheath;

a drive wire passed through the sheath;

a connection hook connected to the distal end of the drive wire;

a base connected to the proximal end of the sheath; and a slider to which the proximal end of the drive wire is connected and which is slidably held against the base in the axial direction of the sheath and the drive wire, the endoscopic treatment tool removably holding a treatment component by means of the connection hook, wherein the base has a guide groove extending in the axial direction and both side walls of the guide groove, and has a plurality of positioning engagement portions that can engage the slider concavo-convexly at a plurality of locations in the axial direction, the slider has, inside a cylindrical body of a predetermined length surrounding the base, a wire fixing portion which is slidably guided into the guide groove and to which the proximal end of the drive wire is fixed, and a concavo-convex engagement portion that is concavo-convexly engaged with one of the plurality of positioning engagement portions when reaching one of the plurality of axial locations relative to the base, and a spring portion with cantilevered structure is integrally provided on at least one of the base and the slider to elastically engage at least one of the plurality of positioning engagement portions of the base and the concavo-convex engagement portion of the slider concavo-convexly with respect to the other.

2. The endoscopic treatment tool according to claim 1, wherein the wire fixing portion and the concavo-convex engagement portion of the slider are formed at different positions from each other in the axial direction of the cylindrical body, when the concavo-convex engagement portion of the slider engages any of the plurality of positioning engagement portions of the base, the wire fixing portion of the slider is slidably guided into the guide groove avoiding the positioning engagement portion of the plurality of positioning engagement portions that engages the concavo-convex engagement portion.

3. The endoscopic treatment tool according to claim 2, wherein the spring portion with cantilevered structure is provided on at least one side of both side wall portions of the guide groove of the base, to be adjacent to the plurality of positioning engagement portions.

4. The endoscopic treatment tool according to claim 1, wherein the wire fixing portion and the concavo-convex engagement portion of the slider protrudes inwardly in the radial direction of the cylindrical body so as to cross each other.

5. The endoscopic treatment tool according to claim 1, wherein for each of the plurality of positioning engagement portions of the base, a spring portion with cantilevered structure is provided on both sides of the axial direction, and each positioning engagement portion is formed by opposing free end portions of the spring portion with cantilevered structure on one side of the axial direction and the spring portion with cantilevered structure on the other side of the axial direction.

6. The endoscopic treatment tool according to claim 5, wherein the spring portion with cantilevered structure on one side of the axial direction and the spring portion with cantilevered structure on the other side of the axial direction corresponding to the respective positioning engagement portions of the base have a curved convex surface protruding toward the inner wall of the cylindrical body of the slider on the respective free end portion side.

7. The endoscopic treatment tool according to claim 1, wherein the spring portion with cantilever structure is provided adjacent to the concavo-convex engagement portion of the slider.

8. The endoscopic treatment tool according to claim 1, wherein the cylindrical body of the slider has a pair of split cylindrical portions, which are opposed to each other in the direction of the depth of the guide groove in the base and are mutually engaged at one end in the axial direction, and a short cylindrical portion that joins the pair of split cylindrical portions at the other end in the axial direction, the pair of split cylindrical portions comprise the wire fixing portion holding the proximal end of the drive wire, and the short cylindrical portion comprises the concavo-convex engagement portion that concavo-convexly engages with any of the plurality of positioning engagement portions of the base.

* * * * *